(12) United States Patent
Hoernig

(10) Patent No.: US 10,699,460 B2
(45) Date of Patent: Jun. 30, 2020

(54) DEPICTION OF MARKERS IN MEDICAL IMAGING

(71) Applicant: Siemens Healthcare GmbH, Erlangen (DE)

(72) Inventor: Mathias Hoernig, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/212,729

(22) Filed: Dec. 7, 2018

(65) Prior Publication Data

US 2019/0180488 A1 Jun. 13, 2019

(30) Foreign Application Priority Data

Dec. 13, 2017 (EP) ..................................... 17206883

(51) Int. Cl.
*G06T 11/60* (2006.01)
*G06T 7/70* (2017.01)
*A61B 90/00* (2016.01)
*A61B 6/12* (2006.01)

(52) U.S. Cl.
CPC ................ *G06T 11/60* (2013.01); *G06T 7/70* (2017.01); *A61B 6/12* (2013.01); *A61B 90/39* (2016.02); *A61B 2090/3937* (2016.02); *A61B 2090/3966* (2016.02); *G06T 2207/10024* (2013.01); *G06T 2207/10048* (2013.01); *G06T 2207/10081* (2013.01); *G06T 2207/10084* (2013.01); *G06T 2207/10088* (2013.01); *G06T 2207/10116* (2013.01); *G06T 2207/10128* (2013.01); *G06T 2207/10132* (2013.01); *G06T 2207/30204* (2013.01); *G06T 2210/41* (2013.01)

(58) Field of Classification Search
None
See application file for complete search history.

(56) References Cited

U.S. PATENT DOCUMENTS

2015/0371390 A1 12/2015 Gassner et al.
2017/0196525 A1* 7/2017 Kim ........................ A61B 90/39
2017/0215823 A1* 8/2017 Ivanov ................... A61B 90/37

FOREIGN PATENT DOCUMENTS

GB 2512384 A 10/2014

OTHER PUBLICATIONS

European Search Report for European Application No. EP17206883 dated Apr. 24, 2018.

* cited by examiner

*Primary Examiner* — Vu Nguyen
(74) *Attorney, Agent, or Firm* — Harness, Dickey & Pierce, P.L.C.

(57) ABSTRACT

A method is disclosed for graphically depicting a marker which is applied to an examination object in an imaging system. In an embodiment, the position of the marker is ascertained by way of a first measuring method. An image of the examination object is provided on the basis of a second measuring method, in which image the position of a graphical object that represents the marker in the image is ascertained and depicted on the basis of the first measuring method.

15 Claims, 3 Drawing Sheets

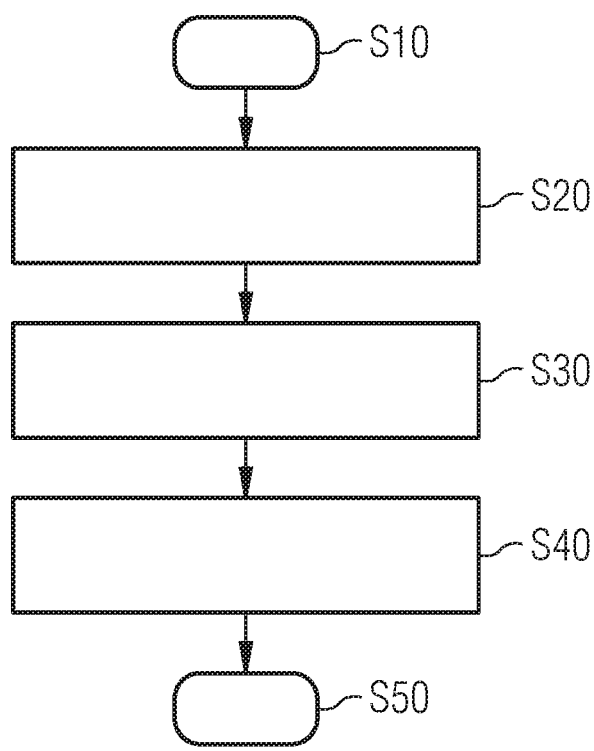

DEPICTION OF MARKERS IN MEDICAL IMAGING

PRIORITY STATEMENT

The present application hereby claims priority under 35 U.S.C. § 119 to European patent application number EP17206883.5 filed Dec. 13, 2017, the entire contents of which are hereby incorporated herein by reference.

FIELD

Embodiments of the present invention generally relate to medical imaging methods, and in particular to a method for depicting a marker in medical imaging methods. Also proposed in example embodiments are a corresponding imaging system, a computer program product and an electronic data medium.

BACKGROUND

In imaging diagnostics, use is often made of physical markers or clips (metal) in order to mark suspicious regions for the examination or to provide alignment aids for positioning purposes. Known examples include metal markers which can be adhered to the breast for suspicious regions in the case of mammography, or metal markers for right/left in the case of radiology for various organs or body regions. Nipple clips for marking the nipple position are a further example, used in the USA in particular. A further example relates to X-ray assisted surgical interventions, wherein regions to be treated are marked (e.g. right, left, ROI).

SUMMARY

The inventors has discovered that one problem associated with such markers, which are usually made of a metal such as lead or surgical steel, is that they produce artifacts in the images. When using image processing algorithms, it is not possible adequately to allow for, detect and separate these high-contrast objects from image data for the body regions. Therefore corrective software is often required in order to minimize these artifacts.

A further problem associated with these so-called object markers and recognized by the inventor, is that the sides (e.g. right, left) might be confused by the user or said markers might be placed incorrectly.

An additional problem recognized by the inventor, is that specific markings could not previously be captured by X-ray imaging and automatically transferred into the diagnostic images. These include e.g. non-metallic markers or marker pencils, which are increasingly used in the context of imaging in order to apply additional information to a person being examined. Likewise, plastic markers cannot be depicted, or clearly depicted, by specific imaging methods. Therefore an important link is missing which would allow the documentation, quality and quality assurance of examinations to be improved for diagnostics, therapy and checkups.

Therefore, in at least one embodiment, an improved method for depicting a marker in medical imaging is required, which does not have the disadvantages cited above.

Further embodiment variants of the invention are described in the claims.

According to a first embodiment of the invention, a method is provided for depicting a marker which is applied to an examination object in an imaging system. In a first step, the position of the marker is ascertained by way of a first measuring method. In a further step, an image of the examination object is provided on the basis of a second measuring method. In an additional step, the position of a graphical object, which represents the marker in the image, is ascertained in the image on the basis of the first measuring method. In a further step, the graphical object is depicted at the ascertained position in the image, wherein the graphical object is not contained in the image of the examination object on the basis of the second measuring method.

According to a further embodiment, an imaging system is provided for depicting a marker which is applied to an examination object, wherein the imaging system comprises a control unit and a memory unit, wherein the memory unit stores control information that can be executed by the control unit, and wherein the imaging system is designed to execute a method of at least one embodiment comprising the following steps when the control information is executed in the control unit. In a first step, the position of the marker is ascertained by way of a first measuring method. In a further step, an image of the examination object is provided on the basis of a second measuring method. In an additional step, the position of a graphical object which represents the marker in the image is ascertained in the image on the basis of the first measuring method. In a further step, the graphical object is depicted at the ascertained position in the image, wherein the graphical object is not contained in the image of the examination object on the basis of the second measuring method.

The imaging system can be designed to execute a method in accordance with the further features described under the first embodiment of the invention when the control information is executed in the control unit.

According to a further embodiment of the invention, provision is made for a computer program product comprising a program that can be loaded directly into a memory of a control unit of an imaging system, having program segments/modules for executing the steps of the method in accordance with the features described under the first embodiment of the invention when the program is executed in the control unit of the imaging system.

According to a further embodiment of the invention, provision is made for an electronically readable data medium on which is stored electronically readable control information that is configured in such a way as to perform the method in accordance with the features described under the first embodiment of the invention when said data medium is used in a control unit of an imaging system.

Using such an imaging system, computer program product and electronically readable data medium, it is possible to achieve technical effects which are comparable to the technical effects described above in respect of the method according to the first embodiment.

BRIEF DESCRIPTION OF THE DRAWINGS

Example embodiments of the invention are explained in greater detail below with reference to the appended drawings.

FIG. 3 shows a flow diagram with steps for performing a method for depicting a marker in accordance with an example embodiment of the invention.

DETAILED DESCRIPTION OF THE EXAMPLE EMBODIMENTS

Figure 1:
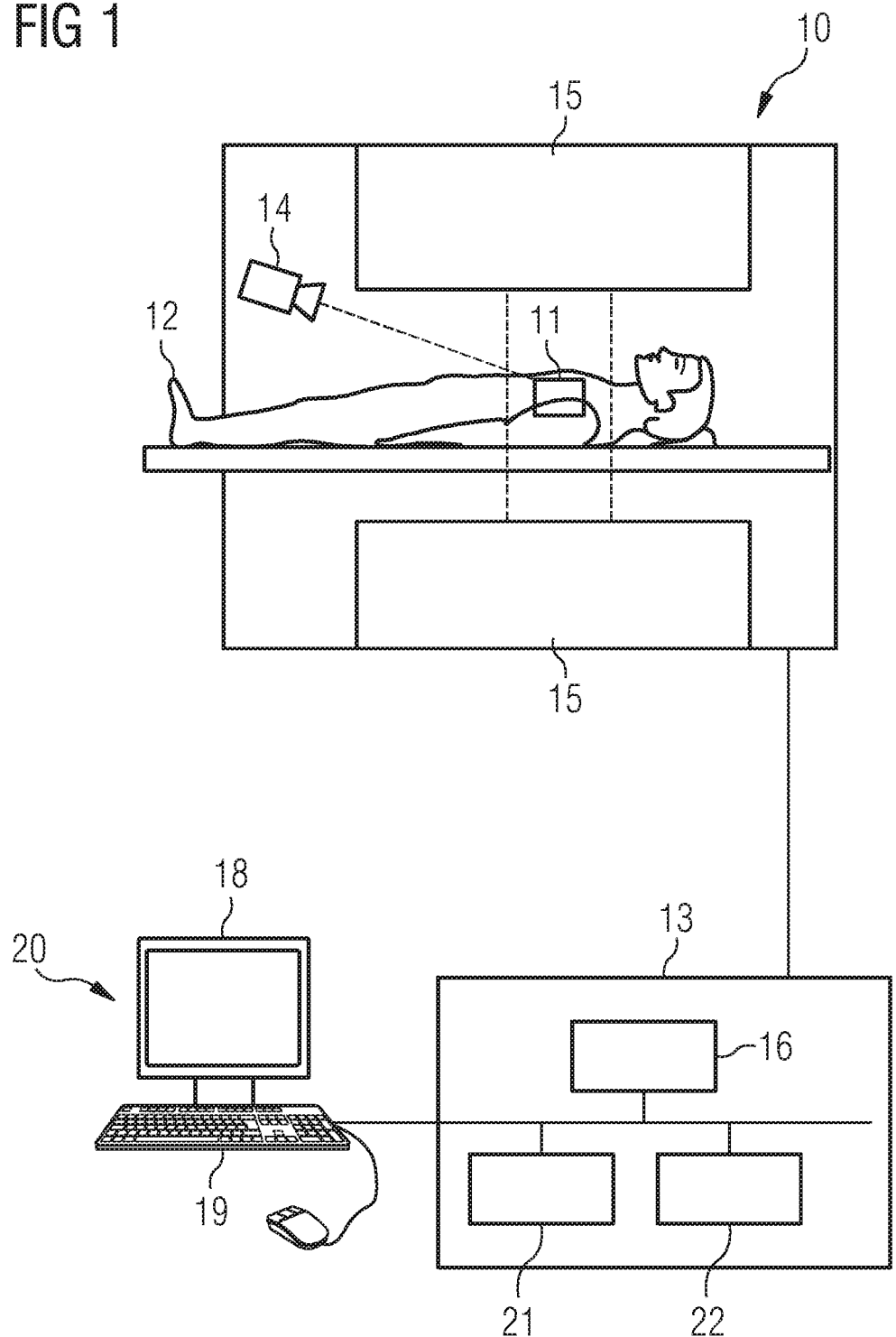
FIG. 1 schematically shows an imaging system by which a method for depicting a marker can be performed according to an embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

According to a first embodiment of the invention, a method is provided for depicting a marker which is applied to an examination object in an imaging system. In a first step, the position of the marker is ascertained by way of a first measuring method. In a further step, an image of the examination object is provided on the basis of a second measuring method. In an additional step, the position of a graphical object, which represents the marker in the image, is ascertained in the image on the basis of the first measuring method. In a further step, the graphical object is depicted at the ascertained position in the image, wherein the graphical object is not contained in the image of the examination object on the basis of the second measuring method.

At least one embodiment of the inventive method has the advantage that errors, e.g. a confusion of sides such as left/right, can be avoided. As a result of using two measuring methods (e.g. two imaging methods) instead of one, it is also possible to improve the accuracy of the positioning and alignment of markings in the examination images, and to improve the image quality, since e.g. non-metallic markers such as lotions and plasters can be used in the X-ray examination, wherein said non-metallic markers cannot be captured by the X-radiation but are nonetheless projected as graphical objects in X-ray images and are therefore visible in the image. As a result of using non-metallic markers, it is possible in particular to avoid artifacts in X-ray images. The overall reliability and quality of examinations and treatments is thereby improved.

Furthermore, such a method can be employed as a quality assurance and documentation method, wherein markers which were applied to a patient during diagnostic or surgical procedures are documented in a patient file and can therefore be used during a check-up or a follow-up examination. A further advantage is that no special hardware is required, since medical imaging systems increasingly have at least two different imaging methods, including in particular optical cameras, e.g. for the locating of detectors or similar components of the imaging system. A further application and use of such integrated cameras is therefore proposed for the clinical procedure and improvement thereof.

In addition to or instead of the spatial position, a spatial orientation or a spatial dimension of the marker can be ascertained, wherein an orientation or a dimension of the graphical object can be correspondingly ascertained in the image such that the graphical object can be depicted in the image.

The first and the second measuring methods can be different measuring methods which are based on different physical measuring principles.

The first and the second measuring methods can be performed at essentially the same time.

The first measuring method can include execution of a voice command of an operator of the imaging system by way of voice recognition.

The depiction of the graphical object can include generating a separate image of the graphical object and superimposing the image of the graphical object on the image of the examination object.

The first measuring method can include image capture via an optical camera, and the second measuring method can include an imaging X-ray method.

According to a further embodiment, an imaging system is provided for depicting a marker which is applied to an examination object, wherein the imaging system comprises a control unit and a memory unit, wherein the memory unit stores control information that can be executed by the control unit, and wherein the imaging system is designed to execute a method of at least one embodiment comprising the following steps when the control information is executed in the control unit. In a first step, the position of the marker is ascertained by way of a first measuring method. In a further step, an image of the examination object is provided on the basis of a second measuring method. In an additional step, the position of a graphical object which represents the marker in the image is ascertained in the image on the basis of the first measuring method. In a further step, the graphical object is depicted at the ascertained position in the image, wherein the graphical object is not contained in the image of the examination object on the basis of the second measuring method.

The imaging system can be designed to execute a method in accordance with the further features described under the first embodiment of the invention when the control information is executed in the control unit.

According to a further embodiment of the invention, provision is made for a computer program product comprising a program that can be loaded directly into a memory of a control unit of an imaging system, having program segments/modules for executing the steps of the method in accordance with the features described under the first embodiment of the invention when the program is executed in the control unit of the imaging system.

According to a further embodiment of the invention, provision is made for an electronically readable data medium on which is stored electronically readable control information that is configured in such a way as to perform the method in accordance with the features described under the first embodiment of the invention when said data medium is used in a control unit of an imaging system.

Using such an imaging system, computer program product and electronically readable data medium, it is possible to achieve technical effects which are comparable to the technical effects described above in respect of the method according to the first embodiment.

The features cited above and features described below can be used not only in the corresponding combinations cited explicitly, but also in further combinations or in isolation without thereby departing from the scope of the present invention.

The properties, features and advantages described above in respect of the invention and the manner in which these are achieved become clearer and easier to comprehend in the context of the following description of the example embodiments, which are described in greater detail with reference to the drawings.

In the context of embodiments of the present invention, imaging methods which are performed by way of imaging systems 10 comprise, as a generic term, various machine-aided examination methods which provide two-dimensional or three-dimensional image data for organs and structures of a person being examined 12, or more generally of an examination object 12.

Depending on the way in which they capture measured data, imaging methods can be based on various physical principles or effects. Measurement data for the generation of images may therefore be captured with the aid of X-radiation (e.g. X-ray recordings, computer tomography), radionuclides (e.g. scintigraphy), ultrasound, nuclear spin resonance (e.g. magnetic resonance tomography), infrared radiation (e.g. diagnostic thermography), or visible light (e.g. endoscopy, optical tomography, video raster stereography).

The choice of an imaging system 10 and/or the imaging measuring method is often based on the requirements for medical diagnosis. For example, bones are depicted effectively in X-ray recordings, scintigraphy can depict inter alia the distribution of activity in the thyroid gland. Most methods produce static recordings. Moving images (including during operations) can be generated by ultrasound, fluoroscopy, endoscopy, and also magnetic resonance tomography, for example.

In the context of embodiments of the present invention, markers 11 are understood to be physical markers, i.e. physical objects or substances which are used to apply additional information to an examination object 12 or patient. Such physical markers comprise objects made of metal, e.g. lead or surgical steel, or plastic, for example, and can likewise comprise plaster markings or markings made by a pencil, marker, or lotion on the person being examined, e.g. on the skin of a patient. Such additional information may be required for the purpose of diagnosis or surgery, for example. In particular, the marker may be selected from a group consisting of a colored marking, an optical marking, an infrared marking, an ultraviolet marking, a laser marking, a specific pattern or a specific shape of the examination object.

FIG. 1 schematically shows an imaging system 10 by which a method for depicting a marker 11 can be performed in accordance with an embodiment of the invention.

A person being examined 12, or more generally an examination object 12, is pushed into the imaging system 10. The imaging system has a first measuring system 14 for performing a first measuring method, and a second measuring system 15 for performing a second measuring method. In FIG. 1, the first measuring system 14 allows an image to be captured via an optical camera, which can operate in the visible range or in the infrared range, and the second measuring system 15 is e.g. an X-ray system. However, any other combination of measuring methods can be implemented for capturing a marker and for generating an image of the examination object, in particular any two imaging methods can be combined with each other. For example, the first measuring system 14 can be an optical or infrared camera system, and the second measuring system 15 an X-ray installation or an MRT installation. Such imaging systems are known to a person skilled in the art and therefore a detailed explanation thereof is not given here.

The imaging system 10 further comprises a control unit 13 which is used to control the imaging system. The central control unit 13, which is designed to perform the method described below for depicting a marker 11, comprises a first controller 21 for the measuring system 14 and a second controller 22 for the measuring system 15. A memory unit 16 can be used to store the control instructions required to record of the examination images, in particular all of the programs required for operation of the imaging system 10. Images can be computed in a computing unit 20 and displayed on a display 18, wherein an operator can operate the imaging system 10 via an input unit 19. The memory unit 16 can have control instructions and program modules which perform the inventive method when executed in the computing unit 20. In particular, the memory unit 16 stores the control information which can be executed by the control unit 13.

According to an embodiment of the invention, the imaging system 10 in FIG. 1 is designed in such a way that, when the control information is executed in the control unit 13, it measures a marker 11 which is attached to the person being examined 12 and depicts said marker as a graphical object 2 in an image 1 of the person being examined 12. In this case, the fundamental idea of an embodiment of the inventive method, which is described in detail in the following, is the depiction of a graphical object in an image 1 of an examination object 12, wherein the measurement of the imaging data and the capture of the marker 11 are performed in different measuring methods.

Figure 2:
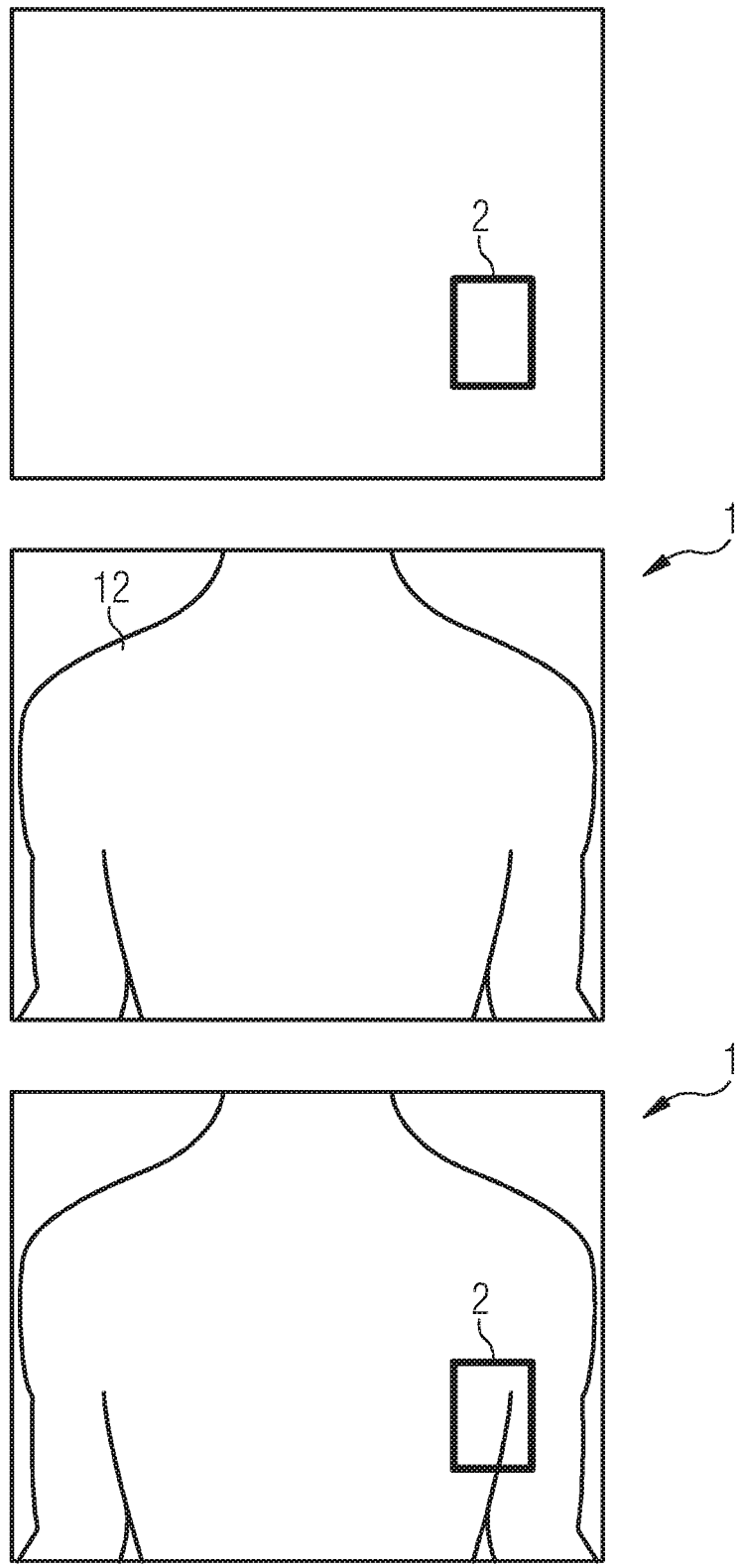
FIG. 2 shows a schematic drawing of a graphical object which is depicted in an image of a person being examined.

FIG. 2 shows a schematic drawing of a graphical object which is depicted in an image 1 of a person being examined.

In the upper part of FIG. 2, the position of a graphical object 2 is shown in an image, wherein said position was ascertained on the basis of a first measuring routine. In the central part of FIG. 2, an image 1 of a person being examined 12 is shown, wherein said image was recorded by way of a second measuring method. A marker 11 that is applied to the person being examined is not depicted in the image 1. In the lower part of FIG. 2, the graphical object 2 is depicted in the image 1 of the person being examined, wherein the position of the graphical object 2 corresponds to the position of the marker 11 on the person being examined 12.

FIG. 3 shows a flow diagram comprising steps for performing a method for depicting a marker 11 in accordance with an example embodiment of the invention.

The method starts in step S10. In step S20, a marker 11 which is applied to a person being examined 12 or more generally to an examination object 12 in an imaging system 10 is captured by way of a first measuring method. In particular, the measured data from the first measuring routine comprises data which is based on the marker 11 and by which it is possible to ascertain characteristics of the marker 11, e.g. a spatial position, a spatial orientation, and a spatial dimension of the marker 11. These characteristics can be ascertained relative to the examination object 11 or also, in another example embodiment, relative to a system of coordinates of the imaging system 10. It is possible in this case for only one characteristic, any desired combination of characteristics, or all of the cited characteristics to be ascertained and subsequently depicted by way of the graphical object 2.

In an example embodiment, the first measuring method also includes capturing a voice command of an operator of the imaging system. The captured voice command can be interpreted by way of voice recognition and executed, such that operator information given verbally or acoustically is input into the first measuring method and also into the selection and generation of a graphical object.

In step S30, an image 1 of the examination object 12 is provided. The image 1 of the examination object 12 is based on measured data from an imaging second measuring method in this case. In an example embodiment, the measured data from the second measuring method essentially comprises no data of the marker 11, i.e. no data which is based on the physical marker 11, although the marker 11 is situated in the field of view of the second measuring method. This can be achieved by suitable selection of the marker with reference to the second imaging method. In another example embodiment, the measured data from the second measuring routine may contain data of the physical marker 11, but this data is not sufficient for the marker 11 to be depicted in the image 1, wherein essentially no artifacts are produced in the image 1 as a result of the marker 11.

In an example embodiment, the first and the second imaging methods are based on different physical measuring principles or in other words on different physical concepts of measurement, i.e. different physical effects. Different measuring principles are known to a person skilled in the art from the DIN 1319 standard, for example. For example, the first measuring method is based on measurement via one of more cameras 14 in the optically visible light range or in the infrared range, and the second measuring method is based on measurement via an X-ray system 15. The first measuring method and the second measuring method can be imaging methods.

In another example embodiment, the first and the second measuring methods are based on the same physical measuring principle, but different measuring routines, or on essentially different measured data. In a further example embodiment, the first measuring method may comprise a subset of the measured data from the second measuring method, e.g. data from an X-ray scan having a specific energy or frequency.

In an example embodiment, the measurements for the first and the second imaging methods are performed at the same time.

In step S40, a graphical object 2 is depicted in the image 1 of the examination object 12. In an example embodiment, the graphical object 2 is not based on the second measuring method, i.e. on the measured data from the second measuring method, and in a further example embodiment is based only on the measured data from the first measuring method. In this context, in an example embodiment, the graphical object 2 is a virtual marking or virtual marker which is ascertained in such a way that it corresponds to the position, orientation or dimension of the marker, i.e. recognizably depicts said marker in the image 1 for an observer. In particular, the graphical object 2 can be depicted in the image 1 in such a way that the position of the graphical object relative to the depicted examination object 12 in the image 1 corresponds to the position of the marker 11 relative to the examination object in the imaging system 10. The same applies to the spatial orientation and the spatial dimension of the graphical object 2 if these were captured by the first measuring method. By this, the marker 11 and the image 1 of the examination object 11 are captured by different measuring methods and recognizably depicted in the image 1 for the user of the imaging system. The method ends in step S50.

In an example embodiment, the depiction of the graphical object 2 may comprise inclusion as an annotation, insertion, projection, or superimposition of the graphical object 2 in or on the image 1 of the examination object 12. Furthermore, the measured data from the first measuring method can be registered with the measured data from the second measuring method, i.e. said data can be associated or linked together.

In an example embodiment, the graphical object 2 can be stored with the image 1 of the examination object 12. In another example embodiment, a separate image of the graphical object 2 is generated and is superimposed on the image 1 of the examination object 12. The image of the graphical object 2 may be stored separately or superimposed on the image 1 of the examination object.

In an example embodiment, the capture of metallic and non-metallic physical markers 11 is effected by way of one or any desired combination of the following example methods: optical or color recognition via e.g. optical cameras, X-ray measurements, spectral X-ray measurements performed in an energy-specific manner, infrared recognition or ultraviolet recognition via a camera, laser, pattern and shape recognition using an optical camera or using X-ray recordings.

In an example embodiment, the capture of the marker 11 or the depiction of the graphical object 2 is based on a selected organ program of the imaging system 10. For example, preselection of possible graphical objects 2 or exclusion of inapplicable graphical objects 2 is effected by following the selected organ program.

In an example embodiment, the capture of the marker 11 or the depiction of the graphical object 2 is based on a comparative object recognition, which can be performed on optical measurements or using X-ray recordings. For example, a handwritten input of an operator is received in the first measuring routine, identified by way of object recognition and assigned to a predetermined graphical object 2.

In an example embodiment, the imaging system 10 is a medical imaging system, a diagnostic system or a therapeutic system. Furthermore, the imaging system can be designed in such a way that, in addition to e.g. the capture of X-ray images, it executes one of the methods cited above, in particular an image analysis of optical images. The system additionally comprises a method for registration of this capture method with the X-ray images. In an example embodiment, the virtual marker (i.e. the graphical object 2) can be trained by a learning algorithm.

In a further example embodiment, the depiction of the graphical object 2 can be trained on the basis of a physical marker 11, in particular with reference to a marking on the skin by e.g. a pencil, a marker pen or a luminescent pen, or further improved in an autonomous self-learning manner. In an example embodiment, for the purpose of capturing a virtual marker in clinical images, in particular for X-ray images, a cream or lotion is applied to the relevant region as a physical marker.

In an example embodiment, the user can tell the system which physical marker 11 or marker type is used, whereupon the system then automatically performs an analysis specifically for the selected type, e.g. the system makes provision for an infrared camera during the analysis if a lotion is used as a marker.

In a further example embodiment, the virtual marker can be embodied as separate image material, e.g. as complete or partially complete optical images, and superimposed on the X-ray images and stored without additional method steps. In an example embodiment, the virtual marker can be captured and documented in 2D or 3D.

In summary, a method is proposed for graphical depiction of a marker which is applied to an examination object in an imaging system. In this case, the position of the marker is ascertained by way of a first measuring method. An image of the examination object is provided on the basis of a second measuring method, in which image the position of a graphical object that represents the marker in the image is depicted on the basis of the first measuring method. In the inventive method, the accuracy of the positioning and alignment of a graphical object, which represents the marker in the image of the examination object, is improved by virtue of two measuring methods.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF REFERENCE SIGNS

1 Image
2 Figure
10 Imaging system
11 Marker
12 Examination object
13 Control unit
14 First measuring system
15 Second measuring system
16 Memory unit
18 Display
19 Input unit
20 Computing unit
21 First controller
22 Second controller

What is claimed is:
1. A method for depicting a marker, applicable to an examination object in an imaging system, the method comprising:
 ascertaining a position of the marker using a first measuring method;
 providing an image of the examination object based upon a second measuring method;
 ascertaining a position of a graphical object based upon the first measuring method, the graphical object representing the marker in the image;
 ascertaining an orientation or a dimension of the marker;
 ascertaining an orientation or a dimension of the graphical object in the image; and
 depicting the graphical object at the ascertained position in the image, wherein the graphical object is depicted with the orientation or the dimension of the graphical object in the image, and the graphical object is not contained in the image of the examination object based upon the second measuring method.

2. The method of claim 1, wherein the first measuring method and the second measuring method are different measuring methods, which are based on different physical measuring principles.

3. The method of claim 2, wherein the first measuring method and the second measuring method are performed at substantially the same time.

4. The method of claim 1, wherein the first measuring method and the second measuring method are performed at substantially the same time.

5. The method of claim 1, wherein the first measuring method includes execution of a voice command of an operator of the imaging system by voice recognition.

6. The method of claim 1, wherein the depicting the graphical object includes generating an image of the graphical object and superimposing the image of the graphical object on the image of the examination object.

7. The method of claim 1, wherein the first measuring method includes image capture via an optical camera and the second measuring method includes an X-ray imaging method.

8. A non-transitory computer program product storing a program, which is directly loadable into a memory of a controller of an imaging system, the program including program segments for executing the method of claim 7 when the program is executed in the controller of the imaging system.

9. A non-transitory electronically readable data medium storing electronically readable control information, the electronically readable control information configured to perform the method of claim 7 when the non-transitory electronically readable data medium is used in a controller of an imaging system.

10. A non-transitory computer program product storing a program, which is directly loadable into a memory of a controller of an imaging system, the program including program segments for executing the method of claim 1 when the program is executed at the controller of the imaging system.

11. A non-transitory electronically readable data medium storing electronically readable control information, the electronically readable control information configured to perform the method of claim 1 when the non-transitory electronically readable data medium is used in a controller of an imaging system.

12. An imaging system for depicting a marker applicable to an examination object, the imaging system comprising:
   a controller; and
   a memory storing control information executable by the controller, wherein the imaging system is configured, upon the control information being executed in the controller, to
   ascertain a position of the marker via a first measuring method,
   provide an image of the examination object based upon a second measuring method,
   ascertain a position of a graphical object based upon the first measuring method, the graphical object representing the marker in the image,
   ascertain an orientation or a dimension of the marker,
   ascertain an orientation or a dimension of the graphical object in the image, and
   depict the graphical object at the ascertained position in the image, wherein
      the graphical object is depicted with the orientation or the dimension of the graphical object in the image, and
      the graphical object is not contained in the image of the examination object based upon the second measuring method.

13. The imaging system of claim 12, wherein the first measuring method and the second measuring method are different measuring methods, based on different physical measuring principles.

14. The imaging system of claim 12, wherein the imaging system is configured, upon the control information being executed in the controller, to depict the graphical object by generating an image of the graphical object and superimposing the image of the graphical object on the image of the examination object.

15. An imaging system, comprising:
   a controller; and
   a memory storing control information executable by the controller, wherein the imaging system is configured, upon the control information being executed in the controller, to
   ascertain a position of a marker via a first measuring method, provide an image of an examination object based upon ea second measuring method,
   ascertain a position of a graphical object based upon the first measuring method, the graphical object representing the marker in the image,
   ascertain an orientation or a dimension of the marker,
   ascertain an orientation or a dimension of the graphical object in the image, and
   depict the graphical object at the ascertained position in the image, wherein
      the graphical object is depicted with the orientation or the dimension of the graphical object in the image,
      the graphical object is not contained in the image of the examination object based upon the second measuring method,
      the first measuring method includes image capture via an optical camera, and
      the second measuring method includes an X-ray imaging method.

* * * * *